United States Patent
Dandiker

(10) Patent No.: US 12,186,326 B2
(45) Date of Patent: Jan. 7, 2025

(54) TESTOSTERONE AND ESTRADIOL TRANSDERMAL SPRAY

(71) Applicant: CELISTA PHARMACEUTICALS LLC, Edina, MN (US)

(72) Inventor: Yogesh Dandiker, Edina, MN (US)

(73) Assignee: CELISTA PHARMACEUTICALS LLC, Edina, MN (US)

( * ) Notice: Subject to any disclaimer, the term of this patent is extended or adjusted under 35 U.S.C. 154(b) by 876 days.

(21) Appl. No.: 17/255,022

(22) PCT Filed: Jul. 3, 2019

(86) PCT No.: PCT/US2019/040510
§ 371 (c)(1),
(2) Date: Dec. 22, 2020

(87) PCT Pub. No.: WO2020/010205
PCT Pub. Date: Jan. 9, 2020

(65) Prior Publication Data
US 2021/0236514 A1    Aug. 5, 2021

Related U.S. Application Data

(60) Provisional application No. 62/694,365, filed on Jul. 5, 2018.

(51) Int. Cl.
| A61K 31/568 | (2006.01) |
| A61K 9/00 | (2006.01) |
| A61K 47/10 | (2017.01) |
| A61K 47/14 | (2017.01) |

(Continued)

(52) U.S. Cl.
CPC .......... *A61K 31/568* (2013.01); *A61K 9/0014* (2013.01); *A61K 47/10* (2013.01); *A61K 47/14* (2013.01); *A61K 47/18* (2013.01); *A61K 47/32* (2013.01)

(58) Field of Classification Search
CPC .... A61K 31/568; A61K 9/0014; A61K 47/10; A61K 47/14; A61K 47/18; A61K 47/32
See application file for complete search history.

(56) References Cited

U.S. PATENT DOCUMENTS

| 6,299,900 B1 | 10/2001 | Reed et al. |
| 6,503,894 B1 | 1/2003 | Dudley et al. |
| 6,750,291 B2 | 6/2004 | Kim et al. |

(Continued)

FOREIGN PATENT DOCUMENTS

| EP | 0712303 B1 | 7/1994 |
| EP | 1322336 A1 | 7/2003 |

(Continued)

OTHER PUBLICATIONS

The International Search Report and The Written Opinion of the International Searching Authority issue date Sep. 20, 2019, in international application No. PCT/US2019/040510.

(Continued)

*Primary Examiner* — Jianfeng Song
(74) *Attorney, Agent, or Firm* — MEDLER FERRO WOODHOUSE & MILLS PLLC

(57) ABSTRACT

The invention relates to a sprayable liquid composition for transdermal delivery of testosterone and/or estradiol, and to methods of treatment using this composition.

5 Claims, 9 Drawing Sheets

(51) Int. Cl.
  *A61K 47/18* (2017.01)
  *A61K 47/32* (2006.01)

(56) References Cited

U.S. PATENT DOCUMENTS

| | | | |
|---|---|---|---|
| 6,803,063 B2* | 10/2004 | Birrenbach | A61Q 17/04 424/60 |
| 6,818,226 B2 | 11/2004 | Reed et al. | |
| 6,923,983 B2 | 8/2005 | Morgan et al. | |
| 6,958,154 B2 | 10/2005 | Andolino Brandt et al. | |
| 6,962,691 B1 | 11/2005 | Lulla et al. | |
| 7,030,104 B2 | 4/2006 | Gray et al. | |
| 7,186,706 B2 | 3/2007 | Rosario-Jansen et al. | |
| 7,214,381 B2 | 5/2007 | Carrara et al. | |
| 8,067,399 B2 | 11/2011 | Lehman et al. | |
| 8,268,346 B2 | 9/2012 | Simes et al. | |
| 8,357,393 B2* | 1/2013 | Morgan | A61K 9/0014 514/872 |
| 8,895,053 B2 | 11/2014 | Grenier et al. | |
| 8,980,309 B2 | 3/2015 | Carrara et al. | |
| 9,078,810 B2 | 7/2015 | Setiawan et al. | |
| 9,180,194 B2 | 11/2015 | Dipietro et al. | |
| 9,289,586 B2 | 3/2016 | Bayly et al. | |
| 2002/0028235 A1 | 3/2002 | Reed et al. | |
| 2004/0013629 A1 | 1/2004 | Andolino Brandt et al. | |
| 2004/0213744 A1 | 10/2004 | Lulla et al. | |
| 2005/0002868 A1 | 1/2005 | Gonda et al. | |
| 2005/0152956 A1 | 7/2005 | Dudley | |
| 2006/0280783 A1 | 12/2006 | Dipietro et al. | |
| 2007/0219171 A1 | 9/2007 | Lulla et al. | |
| 2009/0075963 A1 | 3/2009 | Levinson et al. | |
| 2009/0099149 A1 | 4/2009 | Liu et al. | |
| 2016/0022820 A1 | 1/2016 | Setiawan et al. | |
| 2016/0250227 A1 | 9/2016 | DiPietro et al. | |
| 2017/0128462 A1 | 5/2017 | Simes et al. | |
| 2017/0157377 A1 | 6/2017 | Chang et al. | |
| 2017/0157378 A1 | 6/2017 | Chang et al. | |
| 2017/0296484 A1* | 10/2017 | Kottayil | A61K 47/32 |

FOREIGN PATENT DOCUMENTS

| | | |
|---|---|---|
| EP | 1896038 A1 | 3/2008 |
| WO | 2000 074684 A1 | 12/2000 |

OTHER PUBLICATIONS

Cappelletti et al., Increasing Women's Sexual Desire: The Comparative Effectiveness of Estrogens and Androgens, Horm. Behav 78: 178-193 (2016).
Davis et al., Testosterone for Low Libido in Postmenopausal Women Not Taking Estrogen, NEJM 359 (19):2005-2017 (2008).
Davis et al., Safety and efficacy of a testosterone metered-dose transdermal spray for treating decreased sexual satisfaction in premenopausal women, Ann. Intern. Med. 148:569-577 (2008).
Evamist® product label found at https://www.accessdata.fda.gov/drugsatfda_docs/label/2008/022014s001lbl.pdf.
Eudragit L 100 and Eudragit S 100 Specification Sheet, Evonik Industries AG (Dec. 2012); pp. 1-7.
Egras, A. and Umland, E., The role of transdermal estrogen sprays and estradiol topical emulsion in the management of menopause-associated vasomotor symptoms, Int. J. Gen. Med. 3:147-151 (2010).
Kathe et al. Film Forming Systems for Topical and Transdermal Drug Delivery, Asian Journal of Pharmaceutical Sciences, 12:487-497 (2017).
Kotiyan et al., Eudragits role as crystallization inhibitors in drug-in-adhesive transdermal systems of estradiol, Eur. J. Pharmaceutics Biopharmaceutics 52:173-180 (2001).
Lu et al., Preparation and Characterization of a Metered Dose Transdermal Spray for Testosterone, Acta Pharmaceutica Sinica 3(6): 392-399 (2013).
Leichtnam et al., Formulation and evaluation of a testosterone transdermal spray, J. Pharmaceutical Sci. 95(8): 1693-1702 (2008).
Malik et al., Episodic transdermal delivery of testosterone, Mol. Pharmaceutics 9:1537-1543 (2012).
Misra et al., Biphasic testosterone delivery profile observed with two different transdermal formulations, Pharmaceut. Res. 14(9): 1264-1268 (1997).
Nicolazzo et al., Synergistic enhancement of testosterone transdermal delivery, J. Controlled Release 103:577-585 (2005).
Schroeder, et al., Delivery of ethinylestradiol from film forming polymeric solutions across human epidermis in vitro and in vivo in pigs, J. Controlled Release 118:196-203 (2007).

* cited by examiner

TESTOSTERONE AND ESTRADIOL TRANSDERMAL SPRAY

RELATED APPLICATIONS

The present application is a national phase of International Appl. No.: PCT/US19/40510, filed on Jul. 3, 2019, which claims priority to 62/694,365, filed Jul. 5, 2018, each of which is incorporated fully herein by reference.

BACKGROUND

The primary hormones produced by the ovaries in women are the female sex hormones, estrogen and progesterone, however, the ovaries also produce the male hormone testosterone. Each of these hormones plays a role in a woman's health, and insufficient levels or the natural decrease that occurs with age can cause or contribute to various conditions or disorders. For example, the decrease of estrogen levels during peri-menopause and menopause often causes hot flashes, vaginal epithelial thinning, dryness, burning, and irritation, dyspareunia, and a decrease in libido. Osteoporosis is another condition that can be caused by decreased or insufficient estrogen.

Women may also experience a decrease in testosterone levels during menopause. This decrease can also contribute to decreased libido, as both estrogen and testosterone modulate women's sexual desire (Cappelletti, M. and Wallen, K., *Horm Behav.* 2016 February; 78: 178-193).

Female hypoactive sexual desire disorder (HSDD) refers to a chronic or ongoing decrease or absence of a woman's sexual desire. A woman's libido, which can fluctuate throughout her life, might decrease when she is under emotional stress or experiencing hormonal changes during pregnancy or menopause. An important characteristic of HSDD is that it causes personal distress. It is the most common female sexual dysfunction and affects about 1 in 10 women. HSDD can occur at any age.

In August 2015, the US Food and Drug Administration approved the first and only medication, Addyi® (flibanserin tablet 100 mg), for the treatment of HSDD in premenopausal women in the US. However, Addyi® is only slightly effective over placebo, having been found to increase the average number of satisfying sexual events per month by 0.5 to 1.

There is evidence that administration of transdermal testosterone can increase libido in women. (See e.g., Davis, S., et al., *Anal. Int. Med.,* 2008 April; 148: 569-577; Davis, S. et al., *N. Engl. J. Med.,* 2008 November; 359:2005-17). However, while pharmaceutical companies have sought to develop androgen therapies for male sexual desire disorders, there is currently no FDA approved androgen therapy to treat HSDD in women. (See Cappelletti, M. and Wallen, K. 2016).

Estradiol (usually administered with progesterone in women having a uterus) is used to treat symptoms of menopause in some women. Other uses of estradiol include prevention of osteoporosis in postmenopausal women, and replacement of estrogen in women with ovarian failure or other conditions that cause a lack of natural estrogen in the body. Estrogen is also used off-label to treat HSDD. Testosterone is also prescribed off-label for the treatment of low sexual desire in women. (See Cappelletti et al., 2016).

Estrogen can be administered systemically as a pill, or through the skin via a transdermal patch (e.g., Vivelle-Dot®) or gel, or locally through a vaginal cream or ring. Estradiol is also available as a transdermal spray (Evamist®, 90 mcL per spray containing 1.53 mg estradiol), but this product is only indicated for the treatment of moderate to severe vasomotor symptoms due to menopause.

There are several testosterone replacement therapy products approved for the treatment of men, including a transdermal gel (Androgel®, Testim®, Fortesta®), transdermal solution (Axiron®), transdermal patch (Androderm®), injection (Delatestryl®, Aveed®) and buccal tablet (Striant®). In addition, other orally ingested tablet and capsule forms of methyltestosterone are available.

The oral ingestion route requires administration of a high testosterone dose due to hepatic first-pass metabolism in the liver, while intramuscular administration is painful and can result in supra-physiological testosterone serum concentrations. Testosterone characteristics such as a relatively low molecular weight and moderate lipophilicity make the transdermal route the most suitable route for the administration of testosterone. However, existing transdermal gel and transdermal solution formulations are inconvenient as they must be applied over large surface areas to achieve target plasma levels.

Unfortunately, existing dosage forms that contain estradiol alone or testosterone alone have various disadvantages, and there is no FDA approved product containing both estradiol and testosterone. In addition, there is currently no FDA approved product to treat HSDD in postmenopausal women. A transdermal formulation containing estradiol and/or testosterone in a convenient, easy to apply, formulation that prevents transference of the active ingredients to others is needed for the treatment of conditions caused by insufficient levels of estrogen or testosterone.

SUMMARY

The invention provides a sprayable solution for the transdermal delivery of testosterone and/or estradiol. The composition contains a film forming excipient, which leaves a film on the skin. This film is washable, meaning that it can be removed from the skin, e.g. with water or soap and water. This film is a barrier that prevents transference of the testosterone and/or estradiol from the spray to others, such as the user's partner or child. In addition, the formulation provides an effective dose of estradiol and/or testosterone in a small volume spray. The invention also provides methods of treating hypoactive sexual desire disorder (HSDD), treating symptoms of menopause, preventing or treating osteoporosis, and providing estrogen replacement, in a woman in need thereof, by administering these compositions.

BRIEF DESCRIPTION OF THE DRAWINGS

The foregoing and other features and aspects of the present invention can be better understood from the following description of embodiments and as illustrated in the accompanying drawings. The accompanying drawings, which are incorporated herein and form a part of the specification, further serve to illustrate the principles of the present invention.

DETAILED DESCRIPTION

Figure 1:
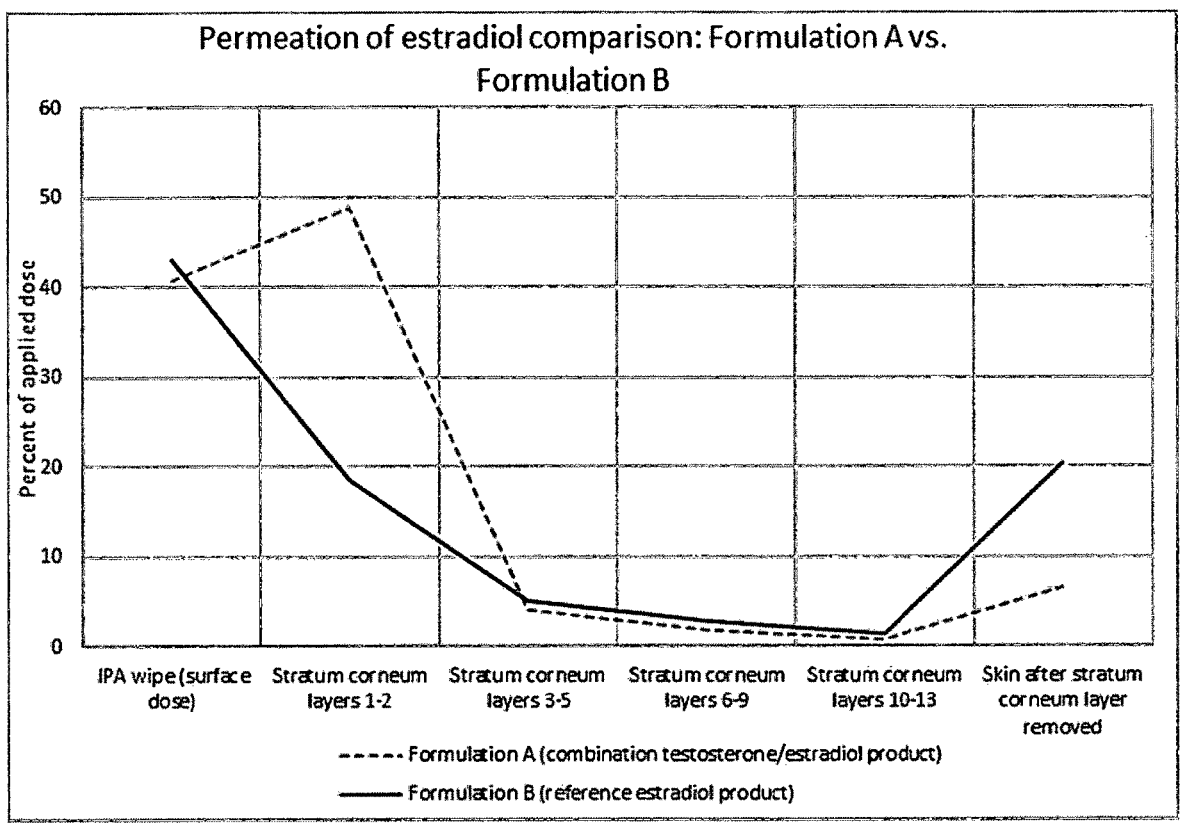
FIG. 1 shows the doses of Estradiol recovered from stripped layers of skin from a tape stripping study performed using porcine skin to compare the Estradiol penetration profile of a film forming formulation containing both Estradiol and Testosterone and including Eudragit® S100 and polyethylene glycol 400 to non-film forming formulations containing estradiol or testosterone.

The present invention is directed to a sprayable liquid solution for the transdermal delivery of testosterone and/or estradiol, and to a method of treatment using this composition. The composition contains a film forming excipient that leaves a film on the skin after the spray has dried. This film is a barrier that prevents transference of the testosterone and/or estradiol from the applied area to others, such as the user's partner or child. This quality provides a large advantage over other topical hormone products.

One disadvantage of transdermal estradiol and testosterone dosage forms is that topical application without a protective cover or barrier over the area may leave unabsorbed drug exposed creating a risk of transfer to other persons.

Transfer of estradiol may cause serious side-effects in others and especially prepubertal children. For example, transfer was found in a study performed to investigate the absorption of estradiol by partners of postmenopausal women after skin-to-skin contact with the application site of an estradiol topical emulsion (Taylor M B, Gutierrez M J, Absorption, bioavailability, and partner transfer of estradiol from a topical emulsion, Pharmacotherapy. 2008 June; 28(6):712-8). In this study, Estradiol was transferred to male partners by means of vigorous skin-to-skin contact at application sites. (Id.) The investigators found a statistically significant increase in post-exposure levels of estradiol in the male partners, although all levels were still below the upper limit of the normal range for men (45 pg/ml). (Id.)

As a result of the risk of secondary estradiol exposure, Evamist® (transdermal spray) is required to display the following black box warning in the approved product label:
Unintentional Secondary Exposure
Breast budding and breast masses in prepubertal females and gynecomastia and breast masses in prepubertal males have been reported following unintentional secondary exposure to Evamist by women using this product. In most cases, the condition resolved with removal of Evamist exposure. Women should ensure that children do not come into contact with the site(s) where Evamist is applied. Healthcare providers should advise patients to strictly adhere to recommended instructions for use.

(See First page of Prescribing Information for Evamist® (rev. November 2017)).

Similar to topical application of estradiol, topical application of testosterone without a protective cover or barrier over the area may leave unabsorbed drug exposed creating a risk of testosterone transfer to other persons. Transfer of testosterone may cause serious side-effects in others, especially prepubertal children.

In fact, topical testosterone creams, gels and solutions are associated with a significant risk for secondary testosterone exposure (Lewis and Goldstein, J Sex Med. 2009 October; 6(10):2649-52). Numerous case reports have demonstrated the occurrence of precocious puberty or virilization in infants and young children following contact with male parents treated with topical testosterone products (Brachet et al., Eur J Pediatr. 2005 October; 164(10):646-7; Bhowmick et al., Clin Pediatr (Phila). 2007 July; 46(6):540-3; Cavender et al., J Sex Med. 2011 February; 8(2):622-6; Kunz et al., Pediatrics. 2004 July; 114(1):282-4; Martinez-Pajares et al., J Pediatr Endocrinol Metab. 2012; 25(9-10): 1007-12; Stephen et al., Endocr Pract. 2008 November; 14(8):1027-30; Yu et al., Pediatrics. 1999 August; 104(2): e23).

Specific changes following secondary testosterone exposure in children include gynecomastia, rapid growth, pubic hair, enlarged penis and clitoris and facial acne (Brachet et al., 2005; Bhowmick et al., 2007; Cavender et al., 2011; Kunz et al., 2004; Lewis and Goldstein, 2009; Yu, 1999). Symptoms generally resolve after exposure to testosterone has ended, although in one case, an enlarged penis persisted in a young boy (Yu, 1999).

As a result of the risk of secondary testosterone exposure, AndroGel® (topical gel) and Axiron® (topical solution) are required to display the following black box warning in the approved product label:

Warning: Secondary Exposure to Testosterone

Virilization has been reported in children who were secondarily exposed to [testosterone gel/topical testosterone products].
Children should avoid contact with unwashed or unclothed application sites in men using [testosterone gel/AXIRON®].
Healthcare providers should advise patients to strictly adhere to recommended instructions for use.

(See First page of Prescribing Information for AndroGel® (rev. October 2016) and Axiron® (rev. July 2017)).

Thus, the ability of the current invention to provide protection from transference of hormones from the composition on the skin of the patient treated to that person's partner or child is a significant advantage.

Another significant advantage of the current invention is that the film is washable, meaning that it can be removed with soap and water. The film will be washed off, e.g., when showering. In other embodiments, the film may be removed with water alone, or with alcohol wipes.

In some embodiments of the invention, the volume of spray administered in a single dose is about 50 µL (microliters), about 100 µL, about 250 µL, or about 300 µL, of solution per actuation. In preferred embodiments, the volume of spray administered is 500 µL or less, 300 µL or less, 250 µL or less, 100 µL or less, or 50 µL or less. In other embodiments, the volume of spray administered is about 25 µL to about 300 µL, about 50 µL to about 300 µL, or about 100 µL to about 250 µL.

In some embodiments, when estradiol is present in the composition, the amount of estradiol administered per actuation is about 0.1 mg to about 25 mg, or about 0.3 mg to about 0.7 mg, or about 0.5 mg. In preferred embodiments, when testosterone is present in the composition, the amount of testosterone administered per actuation is about 0.5 mg to about 25 mg of testosterone, or about 2 mg to about 7 mg, about 3 mg or about 5 mg. For example, in preferred embodiments, the volume of spray administered in a single dose (actuation) may be about 50 µL of solution containing about 0.5 mg estradiol and/or about 3 mg testosterone, or may be about 100 µL of solution containing about 0.5 mg estradiol and/or about 3 mg testosterone, or may be about 250 µL of solution containing about 0.5 mg estradiol and/or about 3 mg testosterone. In some embodiments, the composition contains estradiol in a concentration of about 1 mg/mL to about 10 mg/mL, preferably about 5 mg/mL, and/or testosterone in a concentration of about 20 mg/mL to about 40 mg/mL, preferably about 30 mg/mL.

A very thin layer of solution is formed on the skin when this spray is applied. In only a few minutes, preferably less than 3 minutes or less than 2 minutes, the solvent/s in the spray evaporate leaving behind a film containing estradiol, testosterone, or both, if both are present in the formulation. During solvent evaporation, the excipients in the spray prevent crystallization of estradiol, testosterone, or both if both are present, and maintain estradiol and/or testosterone in an amorphous state during and after solvent evaporation. This is important for penetration of these active ingredients into the skin. Due to this characteristic, it is possible to incorporate unexpectedly high concentrations of estradiol and/or testosterone in the formulation. Whether a composition has this characteristic can be evaluated, for example, using the method described in Example 9.

Within about 5 minutes, or preferably in less than 3 minutes, the estradiol and/or testosterone are absorbed into the skin. The skin then acts as a reservoir from which these active ingredients are released into the systemic circulation over time.

In some embodiments, the formulation according to the invention is packaged as a bulk solution containing multiple doses in a pump spray system comprising a sealed container fitted with a spray pump, preferably a metering spray pump.

Preferably, the pump system is a pump action spray. Pump action sprays require the application of external pressure for actuation, for example, external manual, mechanical or electrically initiated pressure.

The container holding the solution may be any suitable container for the particular composition, such as a glass, polyethylene, aluminum or steel bottle or canister, or an aluminum pouch within a high density polyethylene bottle. The bottle or canister may be lined with an inert material. The spray pump system may also include a dose indicator or dose counter.

The composition of the invention comprises estradiol and/or testosterone, with one or more film forming excipients, one or more penetration enhancers, and one or more solvents. The composition may also contain one or more additional ingredients, such as one or more washability enhancers, viscosity increasing agents and/or fragrances.

The film forming excipient is an excipient, preferably a polymer, that is soluble in aliphatic solvents, preferably in ethanol or a mixture of ethanol with other solvents. The film forming excipient is also soluble in aqueous solutions, preferably water. Although, for film forming excipients having pH dependent solubility, the pH of the aqueous solution must be above or below the specific trigger pH for that excipient to dissolve. For example, some of these film forming excipients dissolve in aqueous solutions only above pH 6.0, only above pH 7.0, or only below pH 5.0. Therefore, soluble in water is defined herein to mean that the film forming excipient has a solubility in water, at the pH required to dissolve that excipient, that requires 30 parts or less of water (solvent) to dissolve one part of the film forming excipient (solute), or more preferably requires 10 parts of water or less to dissolve one part of the film forming excipient. Thus, the film forming excipient has a solubility in water, at a pH between 1 and 10, that requires 30 parts or less of water (solvent) to dissolve one part of the film forming excipient (solute). For example, the film forming excipient has a solubility requiring 30 parts or less of water (solvent) to dissolve one part of the film forming excipient (solute), when the pH of the water is selected from the group consisting of: below pH 5.0, above pH 4, above pH 5, above pH 5.5, above pH 6, and above pH 7.

In addition, preferably the film forming excipient has a solubility in ethanol that requires 30 parts or less of ethanol (solvent) to dissolve one part of the film forming excipient (solute), or more preferably requires 10 parts or less of ethanol to dissolve one part of the film forming excipient. Solubility is evaluated at room temperature.

Where the film forming excipient is a mixture of excipients, the mixture should have the desired characteristics described above.

Some film forming excipients do not have the desired characteristics. For example, occlusive films such as Tegaderm® and Solugel® do not have all of these characteristics.

Examples of film forming excipients that have the desired characteristics include polyacrylates, such as Eudragit® L100 (Methacrylic Acid and Methyl Methacrylate Copolymer 1:1) (which dissolves above pH 6.0), Eudragit® S100 (Methacrylic Acid and Methyl Methacrylate Copolymer 1:2) (which dissolves above pH 7.0), Eudragit® E100 (Poly (butylmethacrylate-co-(2-dimethylaminoethyl)methacrylate-co-methyl methacrylate 1:2:1) (which dissolves below pH 5.0), and celluloses, such as Hypromellose, Hydroxypropyl Cellulose, and Ethyl Cellulose.

In some embodiments of the invention, the concentration of the one or more film forming excipients in the composition is from about 1% w/w to about 10% w/w, from about 2% w/w to about 8% w/w, or from about 3% w/w to about 7% w/w.

When the film forming excipient is an excipient that requires a certain pH to dissolve in water or an aqueous environment, such as Eudragit® S100, a washability enhancer can be included in the composition to make the film more washable, i.e., easier to remove from skin with water or soap and water. In some cases, the washability enhancer also acts as a plasticizer. In one embodiment, the washability enhancer is a low molecular weight polyethylene glycol (PEG) containing two-to-four ethylene glycol units per polymer unit, such as polyethylene glycol 300, 400 or 600.

The concentration of washability enhancer in the composition is about 2% w/w to about 30% w/w, about 5% w/w to about 25% w/w, or about 10% w/w to about 20% w/w, of the weight of the film forming excipient in the composition.

The composition also contains one or more penetration enhancers such as Azone, Glycerol Monooleate, Isopropyl Myristate, Octisalate, Oleic Acid, and/or Transcutol.

In some embodiments of the invention, the concentration of the one or more penetration enhancers in the composition is from about 1% w/w to about 10% w/w, from about 2% w/w to about 8% w/w, or preferably from about 3% w/w to about 7% w/w.

The composition also contains one or more solvents such as Acetone, Ethanol, and/or Isopropyl Alcohol.

In some embodiments of the invention, the concentration of the one or more solvents in the composition is from about 50% w/w to about 95% w/w. In other embodiments of the invention, the solvent is a mixture of ethanol and isopropyl alcohol, and the concentration of ethanol is from about 30% w/w to about 95% w/w, or from about 40% w/w to about 65% w/w, and the concentration of isopropyl alcohol is from about 10% w/w to about 40% w/w, or from about 20% w/w to about 35% w/w. In other embodiments, the composition contains about 70% w/w to about 98% w/w ethanol.

In addition, the composition may contain one or more organic amine proton acceptors such as tromethamine. The concentration of the organic amine proton acceptor is about 0.05 g/L to about 0.2 g/L. Here, grams per liter (g/L) refers to grams of organic proton acceptor per liter ethanol in the composition. In some embodiments, the concentration of the organic amine proton acceptor is about 0.05 g/L, about 0.1 g/L, or about 0.2 g/L. In some embodiments of the invention the solvent contains Tromethamine.

The composition may also include one or more plasticizers such as Dibutyl Sebacate, Triethyl Citrate, Triacetin, Glycerol, a low molecular weight Polyethylene Glycol, e.g., Polyethylene Glycol 300, 400 or 600, and/or Propylene Glycol. The concentration of plasticizer in the composition is about 2% to about 30%, about 5% to about 25%, or about 10% to about 20%, of the weight of the film forming excipient in the composition. Preferably it is about 10% or about 20% of the weight of the film forming excipient in the composition.

The composition of the present invention may also include other formulation excipients, added, e.g., to achieve a desired consistency or appearance, or to protect the formulation components from degradation and oxidation. Such excipients include, for example, viscosity increasing agents, pH adjusting agents, stabilizing agents, antioxidants, humectants, preservatives, colorant and fragrance agents known in the art of formulation.

Viscosity increasing agents that might be included in the formulation are, e.g., Povidone, Glycerin, Hydroxypropyl Cellulose, Methylcellulose, and/or Carboxymethylcellulose. The concentration of the viscosity increasing agent, if included, may be from about 0.5% w/w to about 3% w/w of the composition, from about 1.0% w/w to about 2.5% w/w, or about 1.5% w/w.

The composition of the present invention may contain a fragrance or perfume to impart a desired aroma, or to mask odors that may be associated with other components of the composition. If a fragrance is included, the concentration is from about 0.01% w/w to about 5% w/w of the composition, preferably from about 0.1% w/w to about 1% w/w, or is about 0.5% w/w.

Any fragrance suitable for application to the skin can be used herein including a wide variety of fragrances and perfumes that are known to those skilled in the art. The particular perfume used is largely a matter of choice, however, the fragrance should be used at a level effective for providing a noticeable aroma to the composition, or for masking undesired aroma of the composition. Also, the fragrance and whatever carriers accompany it should not impart excessive stinging to the skin, especially broken or irritated skin.

Typical fragrances are described in Arctander, Perfume and Flavour Chemicals (Aroma Chemicals), Vol. I and II (1969, Allured Publishing Corporation, 1969 (ISBN 0931710375, 9780931710377), and Arctander, Perfume and Flavor Materials of Natural Origin (1994, by Allured Pub Corp) (ISBN 0931710367; ISBN13: 9780931710360). Fragrance used in the present invention may also contain solubilizers, diluents, or solvents which are well known in the art.

One embodiment of the invention is a composition comprising about 0.01% w/w to about 10% w/w estradiol USP, about 0.1% w/w to about 25% w/w testosterone USP; one or more penetration enhancers; one or more solvents; and one or more film forming excipients, wherein the film forming excipient (i) has a solubility in water, at a pH between 1 and 10, that requires 30 parts or less of water to dissolve one part of the film forming excipient, and (ii) has a solubility in ethanol that requires 30 parts or less of ethanol to dissolve one part of the film forming excipient; and wherein the composition is a sprayable liquid solution that forms a washable film when sprayed on skin, and wherein said composition can prevent crystallization of said estradiol and said testosterone when said composition is applied to skin.

In one embodiment, (i) the concentration in the composition of estradiol is about 0.1% w/w to about 5% w/w, the concentration of testosterone in the composition is about 1% w/w to about 10% w/w, (ii) the one or more penetration enhancers is selected from the group consisting of Azone, Glycerol Monooleate, Isopropyl Myristate, Octisalate, Oleic Acid, and Transcutol, (iii) the one or more solvents is selected from the group consisting of Acetone, Ethanol and/or Isopropyl Alcohol, and (iv) the one or more film forming excipients is selected from the group consisting of Eudragit® L100 (Methacrylic Acid and Methyl Methacrylate Copolymer 1:1), Eudragit® S100 (Methacrylic Acid and Methyl Methacrylate Copolymer 1:2), Eudragit® E100 (Poly(butylmethacrylate-co-(2-dimethylaminoethyl)methacrylate-co-methyl methacrylate 1:2:1), Hypromellose, Hydroxypropyl Cellulose, and Ethyl Cellulose.

In other embodiments, the compositions above contain estradiol but do not contain testosterone, or contain testosterone, but do not contain estradiol.

In one embodiment, the composition comprises more than 0.1% w/w estradiol, and more than 1% w/w of testosterone. In some embodiments, the concentration of estradiol in the composition is from about 0.01% w/w to about 10% w/w estradiol USP, or more preferably, is from about 0.1% w/w to about 5% w/w. In preferred embodiments of the invention, the concentration of estradiol is from about 0.1% w/w to about 0.7% w/w. In other preferred embodiments of the invention, the concentration of estradiol is about 5 mg/mL.

In some embodiments, the concentration of testosterone in the composition is from about 0.1% w/w to about 25% w/w, or more preferably, is from about 1% w/w to about 10% w/w. In preferred embodiments of the invention, the concentration of testosterone is from about 1% w/w to about 7% w/w. In other preferred embodiments of the invention, the concentration of testosterone is about 30 mg/mL.

In one embodiment, the invention is a composition comprising estradiol, testosterone, octisalate and methacrylic acid and methyl methacrylate copolymer (1:2) (EUDRAGIT® S100), wherein the composition is a liquid. In other embodiments, this composition contains estradiol but not testosterone, or testosterone, but not estradiol.

In one embodiment, the composition comprises from about 0.1% w/w to about 5% w/w estradiol USP, about 1% w/w to about 10% w/w testosterone USP, about 30% w/w to about 95% w/w ethanol USP, about 10% w/w to about 60% w/w isopropyl alcohol USP, about 1% w/w to about 10% w/w octisalate USP, and about 1% w/w to about 10% w/w Eudragit® S100 USP/NF Methacrylic Acid and Methyl Methacrylate Copolymer 1:2). In other embodiments, this composition contains estradiol but not testosterone, or testosterone, but not estradiol.

In some embodiments of the invention, the composition comprises from about 0.1% w/w to about 5% w/w estradiol USP, about 1% w/w to about 10% w/w testosterone USP, from about 40% w/w to about 65% w/w ethanol USP, from about 20% w/w to about 30% w/w isopropyl alcohol USP, from about 3% w/w to about 7% w/w octisalate USP, and from about 3% w/w to about 7% w/w Eudragit® S100 USP/NF (methacrylic acid and methyl methacrylate copolymer (1:2)). In other embodiments, this composition contains estradiol but not testosterone, or testosterone, but not estradiol.

In another embodiment, the composition comprises from about 0.1% w/w to about 5% w/w estradiol USP, about 1% w/w to about 10% w/w testosterone USP, about 60% w/w to about 98% w/w ethanol USP, about 0.05 g/L to about 0.2 g/L tromethamine (grams tromethamine per liter of ethanol in the composition), about 1% w/w to about 10% w/w octisalate USP, about 1% w/w to about 10% w/w Eudragit® S100 USP/NF Methacrylic Acid and Methyl Methacrylate Copolymer (1:2), and polyethylene glycol 400 in a concentration of about 2% to about 30% of the weight of the Methacrylic Acid and Methyl Methacrylate Copolymer (1:2) in the composition. In other embodiments, this composition contains estradiol but not testosterone, or testosterone, but not estradiol.

In one embodiment, the concentration of estrogen in the composition is about 5 mg/ml, the concentration of testosterone in the composition is about 30 mg/mL, the concentration of octisalate in the composition is about 3% to about 7% w/w, and the concentration of Methacrylic Acid and Methyl Methacrylate Copolymer (1:2) (EUDRAGIT® S100) in the composition is about 3% w/w to about 7% w/w. In other embodiments, this composition contains estradiol but not testosterone, or testosterone, but not estradiol.

The composition is a liquid at room temperature and is sprayable, meaning that the viscosity of the composition allows it to be applied using a spray pump at room temperature. In one embodiment, the composition is contained in a container comprising a spray pump with metering valve. In one embodiment, the viscosity of the composition is less than about 200 cPs, less than about 50 cPs, less than about 20 cPs, less than about 15 cPs, or less than about 10 cPs. Preferably the viscosity of the composition is about 1 cPs to about 20 cPs. Alternatively, the viscosity of the composition is about 15 cPs to about 45 cPs, or is about 7 cPs, about 8 cPs, about 9 cPs, about 10 cPs, about 11 cPs or about 12 cPs. Viscosity is measured using a viscometer such as a Brookfield Viscometer.

The invention also provides a method of treating hypoactive sexual desire disorder (HSDD) in a human female, comprising spraying on the skin of the human female this composition. In some embodiments the female is premenopausal. In some embodiments the female is postmenopausal. In some embodiments the female is perimenopausal.

In addition, the invention provides a method of treating symptoms of menopause by spraying onto the skin of a human female the composition of the invention, where the human female is premenopausal, perimenopausal or postmenopausal, and where the human female has one or more symptoms of menopause selected from the group consisting of hot flashes, vaginal dryness, vaginal burning, and vaginal irritation. In addition, the invention provides a method of treating moderate to severe vasomotor symptoms due to menopause comprising spraying the composition of the invention on the skin of a human female in need of treatment of moderate to severe vasomotor symptoms due to menopause.

The invention also provides a method of preventing or treating osteoporosis, comprising spraying on the skin of a human female the composition of the invention, where the human female is premenopausal, perimenopausal or postmenopausal, and where the composition is administered to prevent or treat osteoporosis.

Moreover, the invention provides a method of providing estrogen replacement, comprising spraying on the skin of a human female the composition of the invention, where the human female suffers from ovarian failure, or lacks natural estrogen in the body.

In preferred embodiments of this method, the amount of estradiol administered in a single application is about 0.5 mg, and/or the amount of testosterone administered in a single application is about 3 mg. In addition, after application of the composition, a barrier film is formed within 3 minutes of application, and this film is capable of preventing transfer of estradiol and testosterone to other persons. This means that less than 5% w/w of the total dose of drug is transferred when the composition is tested by the method described in Example 6.

The film formed on the skin is water washable. This can be evaluated, e.g., by the method described in Example 7.

The film is also breathable. Breathability is the ability of a material to allow moisture vapor to transmit through the material. Breathability tests measure the rate at which moisture vapor moves from a high humidity environment on one side of a material to a low humidity environment on the opposing side. Breathability measurements correlate with actual use of products, for example, bandages that are not breathable can trap moisture against the skin causing poor adhesion or skin irritation. For film forming formulations the film is evaluated for breathability after application to a porous substrate. Since the porous substrate itself has a measurable breathability, the breathability of the film is calculated as a ratio of the breathability of the sample film to the breathability of the substrate without an applied film.

Breathability is a continuous property in that material can range from low breathability to high breathability, and a material's tendency to trap moisture will increase as breathability decreases. The substrate used for the breathability test is porous surgical tape (Transpore™, 3M, St. Paul, Minn.). In addition to serving as a substrate to hold the film, this surgical tape also serves as a reference in that it is a consumer product marketed as a breathable material. Measuring the relative change in moisture vapor transmission rate for the film applied to this substrate gives a practical comparison to a breathable material.

The film formed by the composition of the invention, when dried on a porous substrate, has a water vapor transmission rate, as a fraction compared to a non-occluded control, not less than 0.50 over a 48 hour period. This is calculated by the equation (sample mean rate-occluded control mean rate)/(non-occluded control mean rate-occluded control mean rate). This can be evaluated, e.g., by the method described in Example 8.

Describing the breathability of a film as a relative transmission rate of not less than 0.5 is an appropriate limit to ensure that the breathability of this surgical tape is not substantially reduced when the film is applied and that the breathability of the film is similar to the breathability of the surgical tape substrate.

In some embodiments of the invention, the composition is administered one to four times per 24 hour period. In a preferred embodiment the composition is administered once per 24 hour period. It is preferred that the additional application/s of the composition is/are applied to a different site on the skin from the previous application/s. However, if the film from a previous application/s is washed off the skin before the composition is applied again, the composition may be applied to the same site as the previous application.

As used herein, unless otherwise specified, all formulation ingredient percentages are described as percent weight by weight (% w/w), which refers to the weight of an ingredient as a percentage of the total composition weight.

As used herein, the term "about" means±10% of the value that this term modifies.

As used herein, the term "room temperature" refers to 20° C.

Several embodiments of the invention are described herein. In addition, the invention is described with reference to the following examples. This invention is not limited to the embodiments or examples described herein. Modifications and variations may suggest themselves and are intended to be within the scope of the appended claims.

EXAMPLES

Example 1

Exemplary testosterone/estradiol spray compositions and a manufacturing process for these compositions are described below:

TABLE 1

| Ingredient | Composition % w/w | | | | | | |
|---|---|---|---|---|---|---|---|
| | 1 | 2 | 3 | 4 | 5 | 6 | 7 |
| Estradiol USP | 0.1 | 0.1 | 0.2 | 0.2 | 0.2 | 0.5 | 0.5 |
| Testosterone USP | 0.6 | 0.6 | 1.2 | 1.7 | 2.0 | 3.0 | 5.0 |
| Ethanol USP | 56.3 | 57.8 | 55.5 | 59.1 | 59.8 | 55.0 | 56.6 |
| Isopropyl Alcohol USP | 30.0 | 29.5 | 27.4 | 25.5 | 25.5 | 25.5 | 25.5 |
| Octisalate USP | 4.0 | 6.0 | 7.0 | 5.0 | 6.0 | 7.0 | 6.0 |
| Eudragit ® S100 USP/NF | 7.0 | 5.0 | 7.0 | 7.0 | 5.0 | 7.0 | 5.0 |
| Polyethylene glycol 400 | 1.5 | 1.0 | 1.2 | 1.5 | 1.0 | 1.5 | 0.9 |
| Fragrance | 0.5 | 0.0 | 0.5 | 0.0 | 0.5 | 0.5 | 0.5 |
| TOTAL | 100.0 | 100.0 | 100.0 | 100.0 | 100.0 | 100.0 | 100.0 |

TABLE 2

| Ingredient | Composition % w/w | | | | | | |
|---|---|---|---|---|---|---|---|
| | 8 | 9 | 10 | 11 | 12 | 13 | 14 |
| Estradiol USP | 0.1 | 0.1 | 0.2 | 0.2 | 0.2 | 0.5 | 0.5 |
| Ethanol USP | 56.9 | 58.3 | 56.7 | 60.8 | 61.5 | 58.0 | 61.6 |
| Isopropyl Alcohol USP | 30.5 | 29.1 | 27.4 | 25.5 | 25.8 | 25.5 | 25.5 |
| Octisalate USP | 4.0 | 6.0 | 7.0 | 5.0 | 6.0 | 7.0 | 6.0 |
| Eudragit ® S100 USP/NF | 7.0 | 5.0 | 7.0 | 7.0 | 5.0 | 7.0 | 5.0 |
| Polyethylene glycol 400 | 1.5 | 1.0 | 1.2 | 1.5 | 1.0 | 1.5 | 0.9 |
| Fragrance | 0.0 | 0.5 | 0.5 | 0.0 | 0.5 | 0.5 | 0.5 |
| TOTAL | 100.0 | 100.0 | 100.0 | 100.0 | 100.0 | 100.0 | 100.0 |

TABLE 3

| Ingredient | Composition % w/w | | | | | | |
|---|---|---|---|---|---|---|---|
| | 15 | 16 | 17 | 18 | 19 | 20 | 21 |
| Testosterone USP | 1.7 | 1.7 | 1.7 | 2.00 | 2.00 | 2.00 | 5.00 |
| Ethanol USP | 55.3 | 56.8 | 55.2 | 58.5 | 60.5 | 56.0 | 57.1 |
| Isopropyl Alcohol USP | 30.0 | 29.5 | 27.4 | 25.5 | 25.5 | 26.0 | 25.5 |
| Octisalate USP | 4.0 | 6.0 | 7.0 | 5.0 | 6.0 | 7.0 | 6.0 |
| Eudragit ® S100 USP/NF | 7.0 | 5.0 | 7.0 | 7.0 | 5.0 | 7.0 | 5.0 |
| Polyethylene glycol 400 | 1.5 | 1.0 | 1.2 | 1.5 | 1.0 | 1.5 | 0.9 |
| Fragrance | 0.5 | 0.0 | 0.5 | 0.5 | 0.0 | 0.5 | 0.5 |
| TOTAL | 100.0 | 100.0 | 100.0 | 100.0 | 100.0 | 100.0 | 100.0 |

Manufacturing Process:

Ethanol and Isopropyl alcohol are mixed in a suitable vessel. Eudragit® S100 and Polyethylene glycol 400 are added to these solvents, and the mixture is stirred until a clear solution is formed. Octisalate and Fragrance are added and the solution is stirred further. Estradiol and/or Testosterone are added to it and the mixture is stirred until a clear solution is achieved. The solution is filled into a suitable container and a spray pump is affixed to the container.

Example 2

Exemplary testosterone/estradiol spray compositions and a manufacturing process for these compositions are described below:

TABLE 4

| Ingredient | Composition % w/w | | | | | | |
|---|---|---|---|---|---|---|---|
| | 22 | 23 | 24 | 25 | 26 | 27 | 28 |
| Estradiol USP | 0.1 | 0.1 | 0.2 | 0.2 | 0.2 | 0.5 | 0.5 |
| Testosterone USP | 0.6 | 0.6 | 1.2 | 1.7 | 2.0 | 3.0 | 5.0 |
| Ethanol USP | 58.1 | 58.2 | 54.2 | 59.4 | 60.7 | 55.9 | 56.9 |
| Isopropyl Alcohol USP | 29.1 | 29.1 | 29.1 | 25.2 | 25.2 | 25.2 | 25.5 |
| Octisalate USP | 4.0 | 6.0 | 7.0 | 5.0 | 6.0 | 7.0 | 6.0 |
| Eudragit ® S100 USP/NF | 7.0 | 5.0 | 7.0 | 7.0 | 5.0 | 7.0 | 5.0 |
| Polyethylene Glycol 300 | 1.1 | 1.0 | 1.4 | 1.5 | 0.9 | 1.4 | 1.1 |
| TOTAL | 100.0 | 100.0 | 100.0 | 100.0 | 100.0 | 100.0 | 100.0 |

TABLE 5

| Ingredient | Composition 29 | 30 | 31 | 32 | 33 | 34 |
|---|---|---|---|---|---|---|
| | % w/w | | | | | |
| Estradiol USP | 0.1 | 0.1 | 0.1 | 0.2 | 0.2 | 0.2 |
| Ethanol USP | 58.6 | 58.8 | 55.4 | 61.1 | 62.7 | 59.2 |
| Isopropyl Alcohol USP | 29.1 | 29.1 | 29.1 | 25.2 | 25.2 | 25.2 |
| Octisalate USP | 4.0 | 6.0 | 7.0 | 5.0 | 6.0 | 7.0 |
| Eudragit ® S100 USP/NF | 7.0 | 5.0 | 7.0 | 7.0 | 5.0 | 7.0 |
| Polyethylene Glycol 300 | 1.2 | 1.0 | 1.4 | 1.5 | 0.9 | 1.4 |
| TOTAL | 100.0 | 100.0 | 100.0 | 100.0 | 100.0 | 100.0 |

TABLE 6

| Ingredient | Composition 35 | 36 | 37 | 38 | 39 | 40 |
|---|---|---|---|---|---|---|
| | % w/w | | | | | |
| Testosterone USP | 1.7 | 1.7 | 1.7 | 2.0 | 2.0 | 2.0 |
| Ethanol USP | 57.1 | 57.2 | 53.7 | 59.3 | 60.9 | 57.4 |
| Isopropyl Alcohol USP | 29.0 | 29.1 | 29.2 | 25.2 | 25.2 | 25.2 |
| Octisalate USP | 4.0 | 6.0 | 7.0 | 5.0 | 6.0 | 7.0 |
| Eudragit ® S100 USP/NF | 7.0 | 5.0 | 7.0 | 7.0 | 5.0 | 7.0 |
| Polyethylene Glycol 300 | 1.2 | 1.0 | 1.4 | 1.5 | 0.9 | 1.4 |
| TOTAL | 100.0 | 100.0 | 100.0 | 100.0 | 100.0 | 100.0 |

Manufacturing Process:

Ethanol and Isopropyl alcohol are mixed in a suitable vessel. Eudragit® S100 and polyethylene glycol 300 are added, and the mixture is stirred until a clear solution is formed. Octisalate is added and the solution is mixed. Estradiol and/or Testosterone are added to it and the mixture is stirred until a clear solution is achieved. The solution is filled into a suitable container and a spray pump is affixed to the container.

Example 3

Exemplary testosterone/estradiol spray compositions and a manufacturing process for these compositions are described below:

TABLE 7

| Composition | 41 | 42 | 43 | 44 |
|---|---|---|---|---|
| Estradiol USP | 5 mg/mL | 5 mg/mL | 5 mg/mL | 5 mg/mL |
| Testosterone USP | 30 mg/mL | 30 mg/mL | 30 mg/mL | 30 mg/mL |
| Vehicle Ingredients | % w/w | | | |
| Ethanol USP with tromethamine | 92.2 (0.1 g tromethamine/L EtOH) | 89.8 (0.1 g tromethamine/L EtOH) | 87.0 (0.1 g tromethamine/L EtOH) | 88.5 (0.1g tromethamine/L EtOH) |
| Octisalate USP | 3.0 | 4.0 | 6.0 | 5.0 |
| Eudragit ® S100 USP | 4.0 | 5.0 | 6.0 | 5.0 |
| Polyethylene glycol 400 | 0.9 | 1.2 | 1.0 | 1.5 |
| Total | 100.0 | 100.0 | 100.0 | 100.0 |

TABLE 8

| Composition | 45 | 46 | 47 | 48 |
|---|---|---|---|---|
| Estradiol USP | 5 mg/ml | 5 mg/ml | 5 mg/ml | 5 mg/ml |
| Vehicle Ingredients | % w/w | | | |
| Ethanol USP with tromethamine | 92.1 (0.1 g tromethamine/L EtOH) | 92.5 (0.1 g tromethamine/L EtOH) | 89.0 (0.1 g tromethamine/L EtOH) | 87.8 (0.1 g tromethamine/L EtOH) |
| Octisalate USP | 3.0 | 4.0 | 5.0 | 6.0 |
| Eudragit ® S100 USP | 4.0 | 3.0 | 5.0 | 5.0 |
| Polyethylene glycol 400 | 0.9 | 0.5 | 1.0 | 1.2 |
| Total | 100.0 | 100.0 | 100.0 | 100.0 |

TABLE 9

| Composition | 49 | 50 | 51 | 52 |
|---|---|---|---|---|
| Testosterone USP | 30 mg/ml | 30 mg/ml | 30 mg/ml | 30 mg/ml |
| Vehicle Ingredients | % w/w | | | |
| Ethanol USP with tromethamine | 92.1 (0.1 g tromethamine/L EtOH) | 90.1 (0.1 g tromethamine/L EtOH) | 86.5 (0.1 g tromethamine/L EtOH) | 88.0 (0.1 g tromethamine/L EtOH) |
| Octisalate USP | 3.0 | 4.0 | 6.0 | 6.0 |
| Eudragit ® S100 USP | 4.0 | 5.0 | 6.0 | 5.0 |
| Polyethylene glycol 400 | 0.9 | 0.9 | 1.5 | 1.0 |
| Total | 100.0 | 100.0 | 100.0 | 100.0 |

Manufacturing Process:

Ethanol, and tromethamine are mixed in a suitable vessel. Eudragit® S100 and polyethylene glycol 400 are added, and the mixture is stirred until a clear solution is formed. Octisalate is added and the solution is mixed. Estradiol and/or Testosterone are added and the mixture is stirred until a clear solution is achieved. The solution is filled into a suitable container and a spray pump is affixed to the container.

Example 4

Exemplary testosterone/estradiol spray compositions and a manufacturing process for these compositions are described below:

TABLE 10

| Composition | 53 | 54 | 55 | 56 |
|---|---|---|---|---|
| Estradiol USP | 5 mg/ml | 5 mg/ml | 5 mg/ml | 5 mg/ml |
| Testosterone USP | 30 mg/ml | 30 mg/ml | 30 mg/ml | 30 mg/ml |
| Vehicle Ingredients | % w/w | | | |
| Ethanol USP with tromethamine | 59.3 (0.1 g tromethamine/L EtOH) | 60.3 (0.1 g tromethamine/L EtOH) | 59.6 (0.1 g tromethamine/L EtOH) | 59.0 (0.1 g tromethamine/L EtOH) |
| Isopropyl Alcohol USP | 29.7 | 27.9 | 26.5 | 28.0 |
| Octisalate USP | 4.0 | 6.0 | 7.0 | 5.0 |
| Eudragit ® S100 USP | 6.0 | 5.0 | 6.0 | 7.0 |
| Polyethylene glycol 400 | 1.0 | 0.8 | 0.9 | 1.0 |
| TOTAL | 100.0 | 100.0 | 100.0 | 100.0 |

TABLE 11

| Composition | 57 | 58 | 59 | 60 |
|---|---|---|---|---|
| Estradiol USP | 5 mg/ml | 5 mg/ml | 5 mg/ml | 5 mg/ml |
| Vehicle Ingredients | % w/w | | | |
| Ethanol USP with tromethamine | 59.0 (0.1 g tromethamine/L EtOH) | 60.1 (0.1 g tromethamine/L EtOH) | 58.0 (0.1 g tromethamine/L EtOH) | 63.1 (0.1 g tromethamine/L EtOH) |
| Isopropyl Alcohol USP | 29.0 | 27.9 | 26.5 | 27.0 |
| Octisalate USP | 5.0 | 6.0 | 7.0 | 5.0 |
| Eudragit ® S100 USP | 6.0 | 5.0 | 7.0 | 4.0 |
| Polyethylene glycol 400 | 1.0 | 1.0 | 1.5 | 0.9 |
| TOTAL | 100.0 | 100.0 | 100.0 | 100.0 |

TABLE 12

| Composition | 61 | 62 | 63 | 64 |
|---|---|---|---|---|
| Testosterone USP | 30 mg/ml | 30 mg/ml | 30 mg/ml | 30 mg/ml |
| Vehicle Ingredients | % w/w | | | |
| Ethanol USP with tromethamine | 59.0 (0.1 g tromethamine/L EtOH) | 60.3 (0.1 g tromethamine/L EtOH) | 58.65 (0.1 g tromethamine/L EtOH) | 63.1 (0.1 g tromethamine/L EtOH) |
| Isopropyl Alcohol USP | 29.0 | 27.9 | 26.5 | 27.0 |
| Octisalate USP | 5.0 | 6.0 | 7.0 | 5.0 |
| Eudragit® S100 USP | 6.0 | 5.0 | 7.0 | 4.0 |
| Polyethylene glycol 400 | 1.0 | 0.8 | 0.85 | 0.9 |
| TOTAL | 100.0 | 100.0 | 100.0 | 100.0 |

Manufacturing Process:

Ethanol, and tromethamine are mixed in a suitable vessel. Isopropyl Alcohol is added and the solution mixed. Eudragit® S100 and polyethylene glycol 400 are added, and the mixture is stirred until a clear solution is formed. Octisalate is added and the solution is mixed. Estradiol and/or Testosterone are added to it and the mixture is stirred until a clear solution is achieved. The solution is filled into a suitable container and a spray pump is affixed to the container.

Example 5: Tape Stripping Study

A Tape Stripping Study was performed to compare the penetration profile of a film forming formulation (Formulation A) to that of non-film forming reference formulations with testosterone (Formulation B) and with estradiol (Formulation C). Formulations A, B, & C, described in the following table, were evaluated in this tape stripping study:

TABLE 13

| Vehicle Ingredients | Formulation A (30 mg/ml testosterone, 5 mg/ml estradiol) | Formulation B (17 mg/ml estradiol) | Formulation C (20 mg/ml testosterone) |
|---|---|---|---|
| Ethanol USP | — | 91.5 | 63.0 |
| 0.1 g/L Tromethamine in Ethanol USP | 90.2 | — | — |
| Isopropyl Alcohol USP | — | — | 28.6 |
| Octisalate USP | 4.0 | 8.5 | 6.0 |
| Eudragit® S100 USP | 5.0 | — | — |
| Polyethylene glycol 400 | 0.8 | — | — |
| Povidone K90 USP | — | — | 2.4 |
| Vehicle Total | 100.0% w/w | 100.0% w/w | 100.0% w/w |

Procedure: Porcine skin was obtained from Stellen Medical and stored in a −20° C. freezer. Skin specimens were placed on a tissue moistened with water on a glass dish heated by a 37° C. water bath. 250 µl of each test formulation was applied to a 20 cm² area of skin surface using a syringe and allowed to dry for 15 minutes. The skin was wiped with a tissue wetted with isopropyl alcohol to remove the surface dose. Layers of the stratum corneum were removed by pressing on pieces of Scotch brand book tape onto the skin and then peeling off the tape. Layers were grouped and extracted into 40 ml of ethanol and analyzed by HPLC. The amounts of testosterone and estradiol (% dose) recovered from each layer, as well as the amount removed by the tissue and the amount in the remaining skin were calculated by comparison to a standard of known concentrations.

Figure 2:
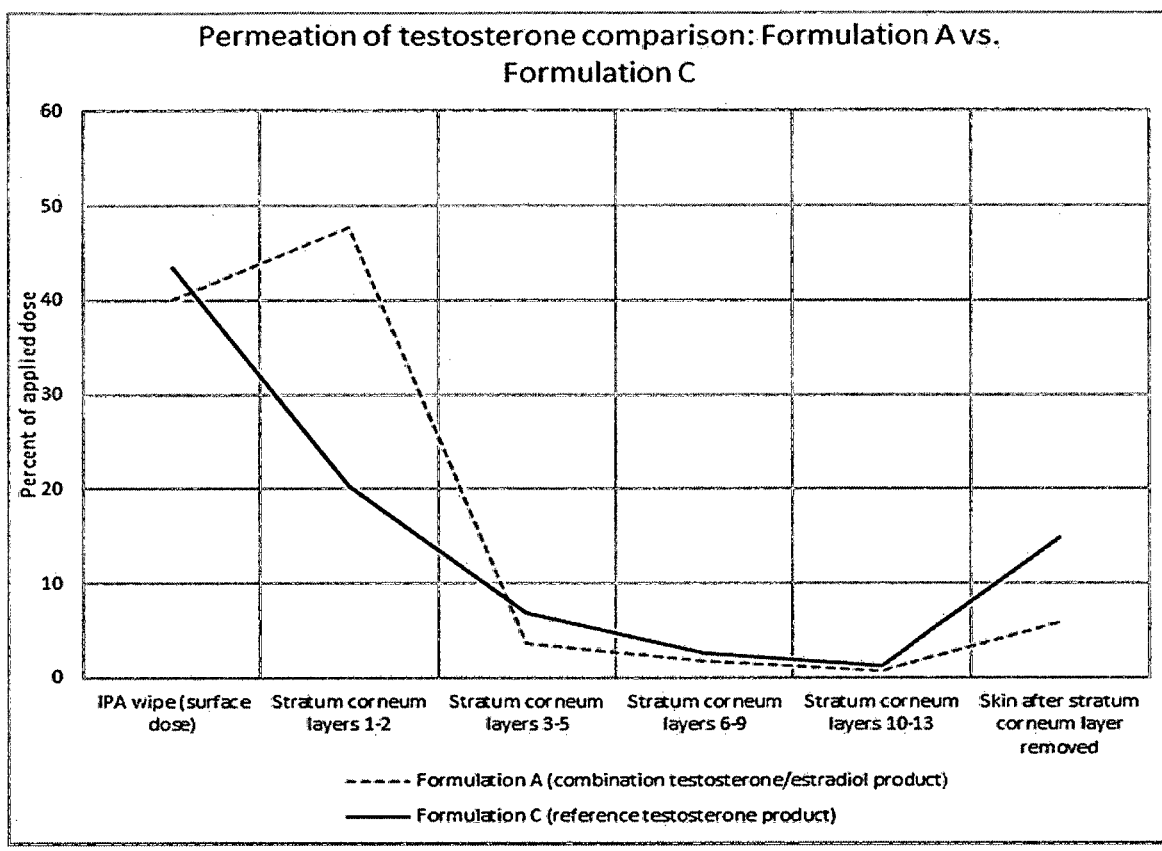
FIG. 2 shows the doses of Testosterone recovered from stripped layers of skin from a tape stripping study performed in porcine skin to compare the Testosterone penetration profile of a film forming formulation containing both Estradiol and Testosterone to non-film forming formulations containing estradiol or testosterone.
Figure 3:
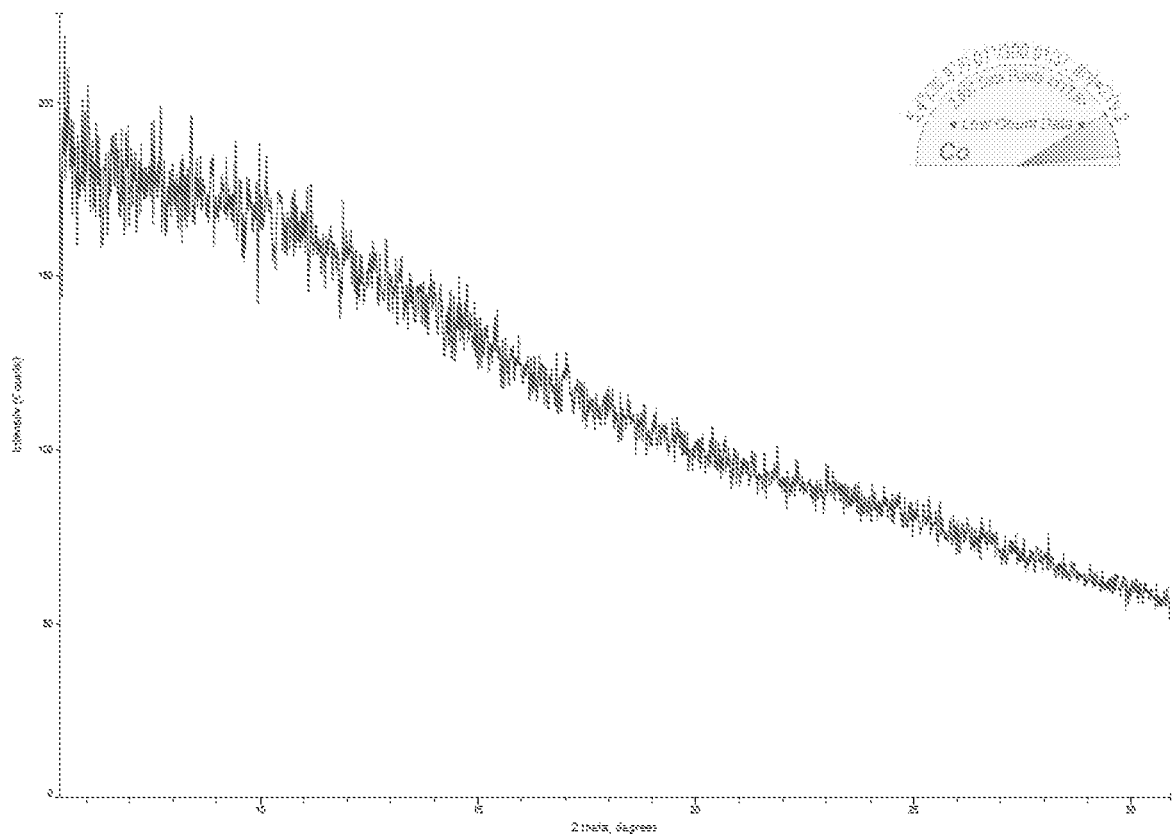
FIG. 3 shows the Two Dimensional Powder X-Ray Diffraction (2DPXRD) Pattern for a Silicon wafer plate without a formulation sample (i.e., background).
Figure 4:
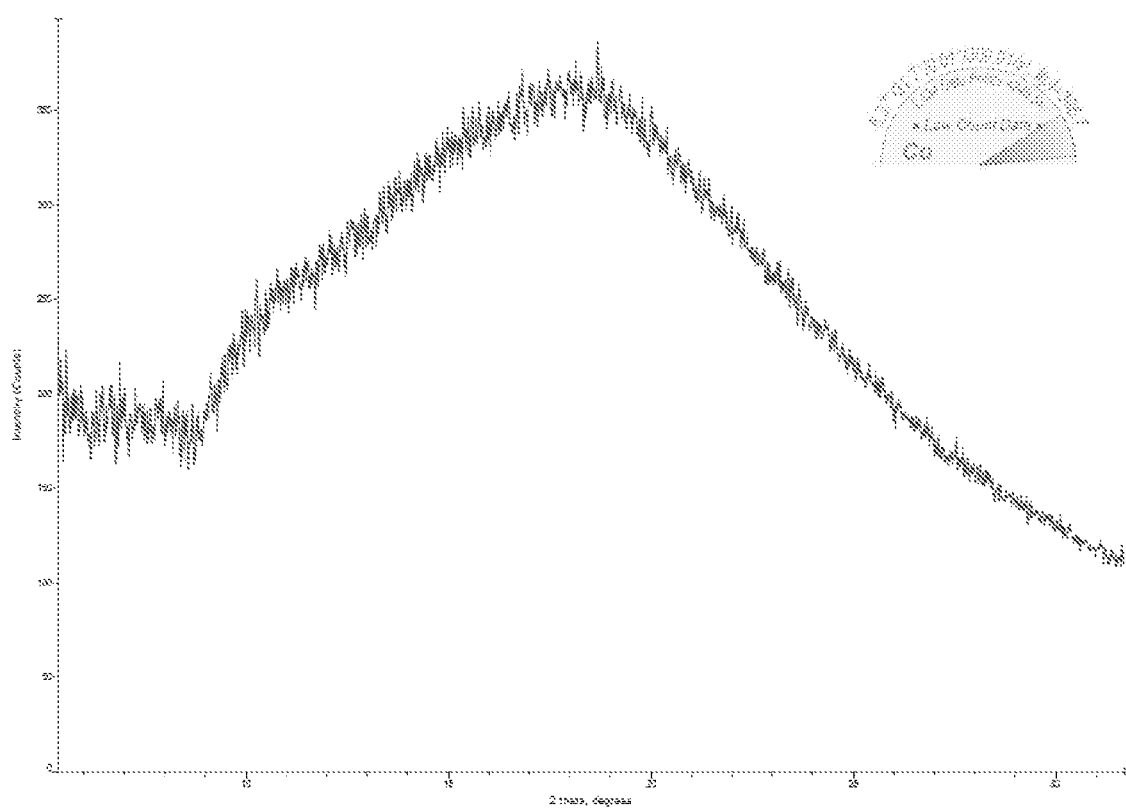
FIG. 4 shows the 2DPXRD Pattern for a plate with a 10 µL sample of Formulation A after storage for 25 minutes under ambient conditions. The sample is amorphous.
Figure 5:
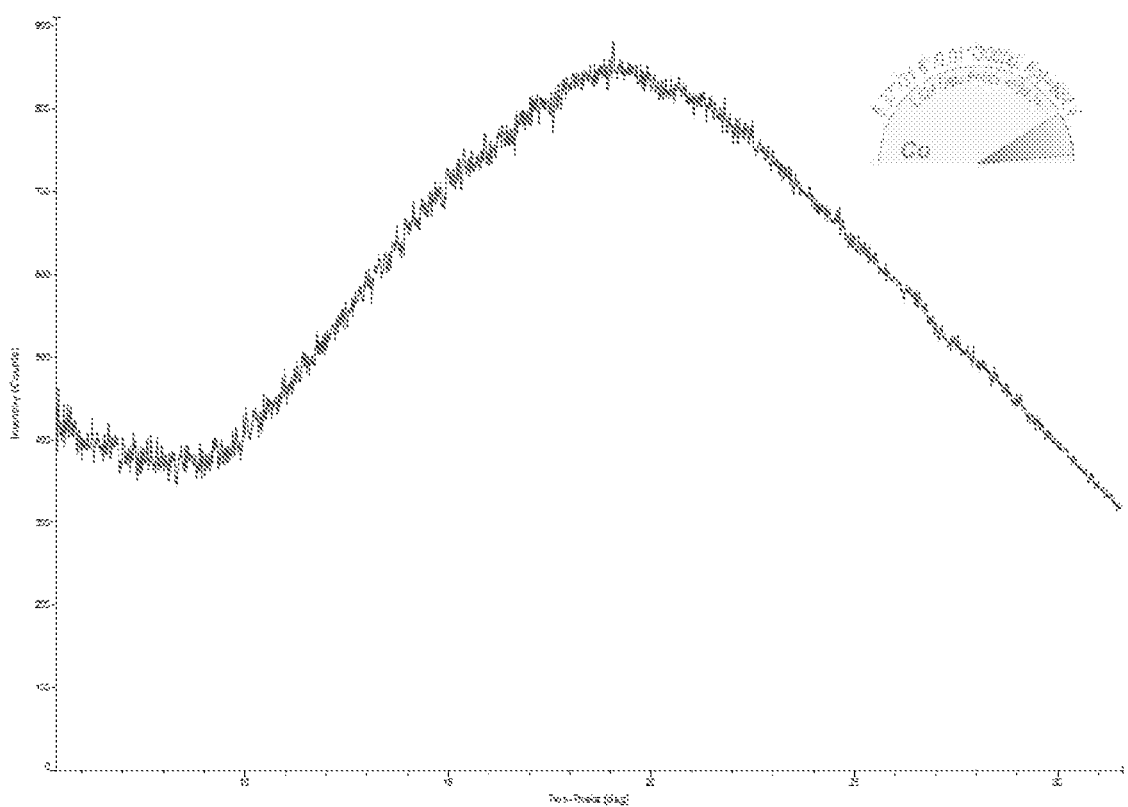
FIG. 5 shows the 2DPXRD Pattern for a plate with a 60 µL sample of Formulation A after storage for 30 minutes under ambient conditions. The sample is amorphous.
Figure 6:
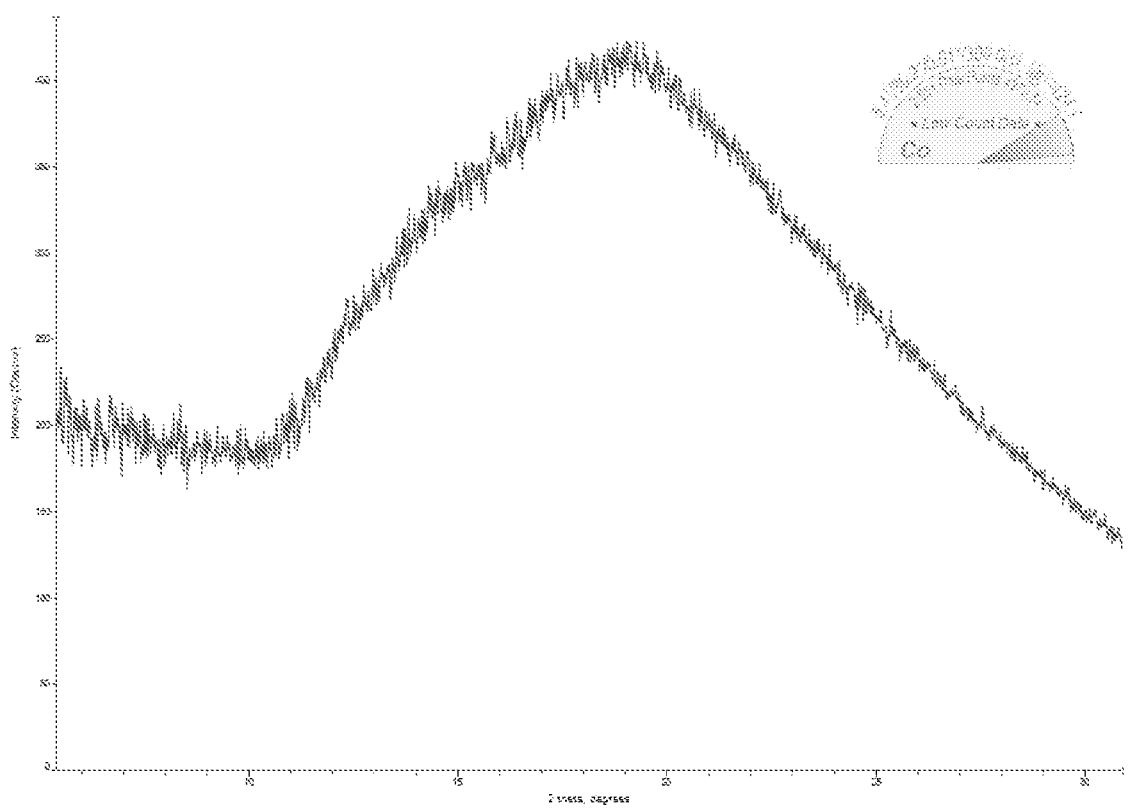
FIG. 6 shows the 2DPXRD Pattern for a plate with a 20 µL sample of Formulation D after storage for 15 minutes under ambient conditions. The sample is amorphous.
Figure 7:
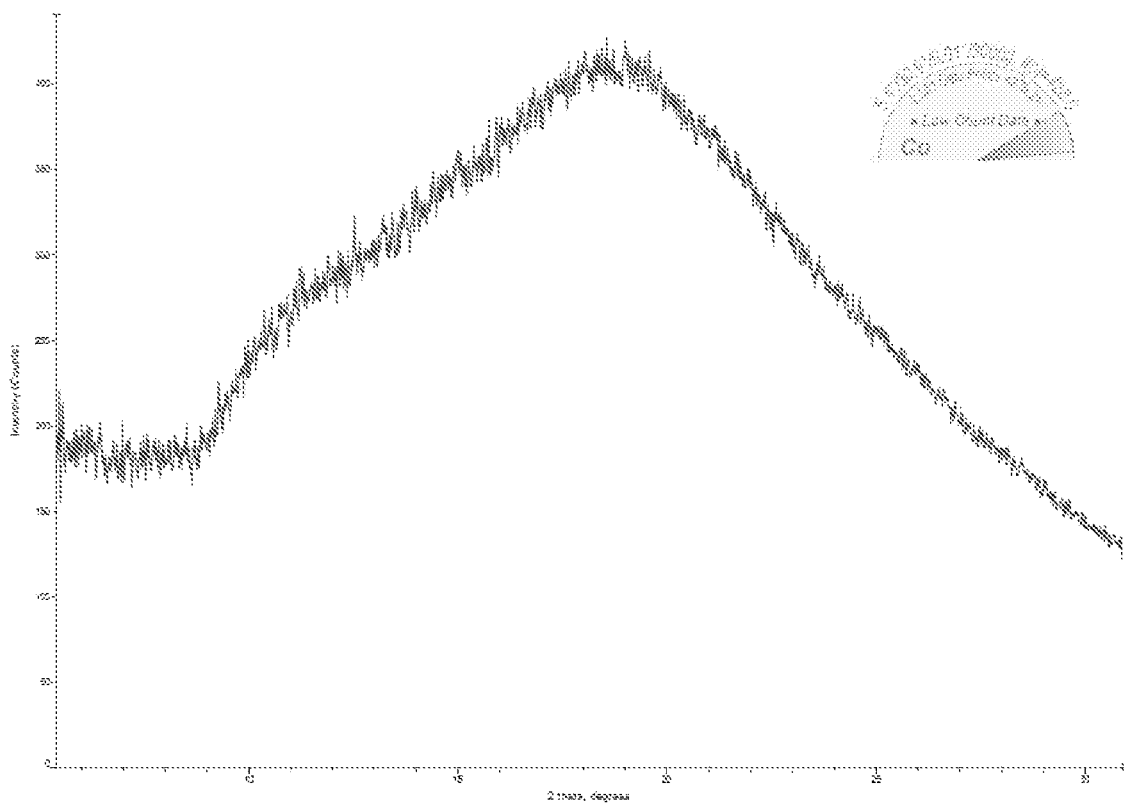
FIG. 7 shows the 2DPXRD Pattern for a plate with a 20 µL sample of Formulation D after storage for 25 minutes under ambient conditions (second time repetition). The sample is amorphous.
Figure 8:
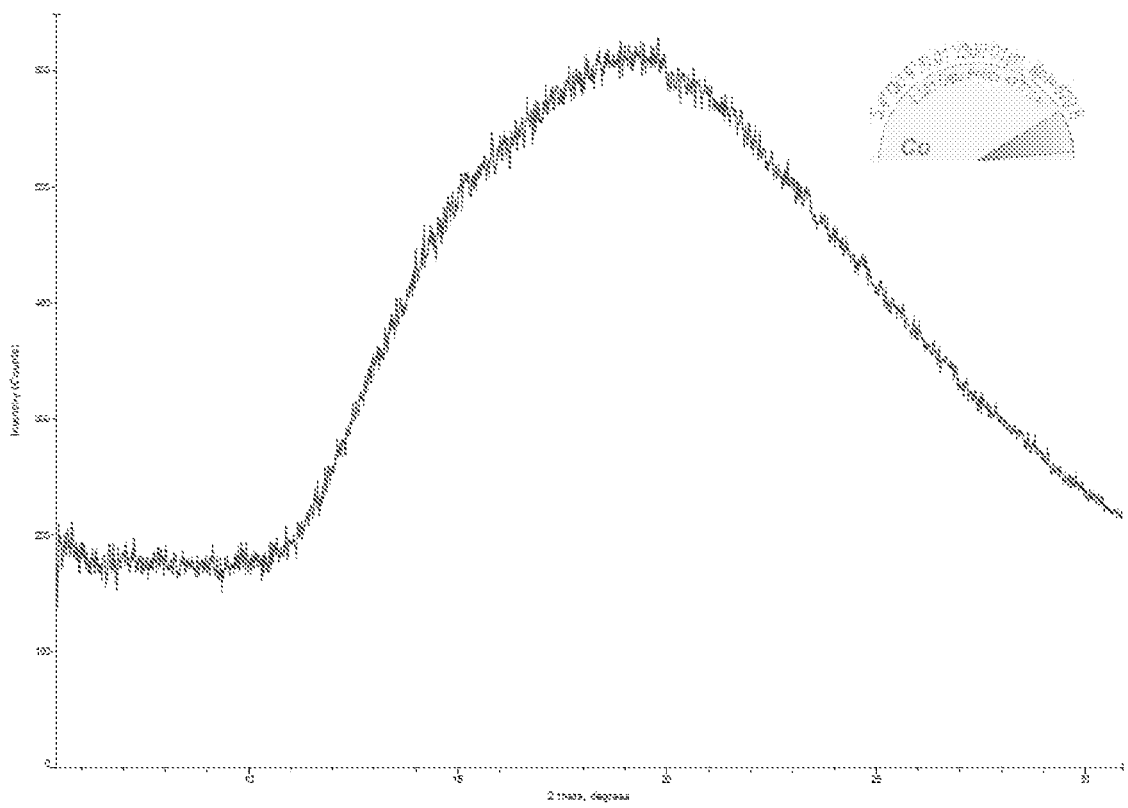
FIG. 8 shows the 2DPXRD Pattern for a plate with a 20 µL sample of Formulation E after storage for 20 minutes under ambient conditions. The sample is amorphous.
Figure 9:
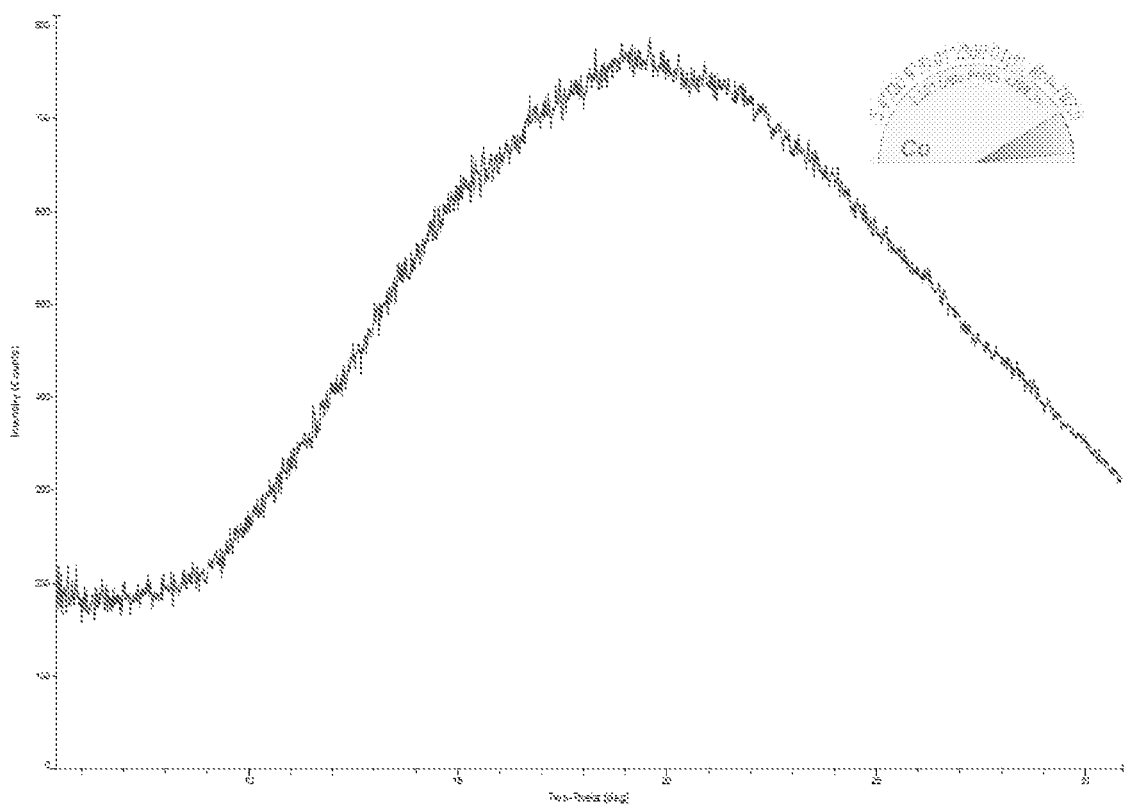
FIG. 9 shows the 2DPXRD Pattern for a plate with a 60 µL sample of Formulation E after storage for 30 minutes under ambient conditions. The sample is amorphous.

The results comparing formulation A to formulation B are depicted in FIG. 1, and the results comparing formulation A to formulation C are depicted in FIG. 2.

Conclusion: Testosterone and estradiol for the film forming formulation are penetrating the stratum corneum indicating that film forming ingredients Eudragit® S100 and polyethylene glycol 400 do not prevent drug penetration.

Example 6: Skin Contact Transfer Study

A skin contact transfer study was performed to compare active ingredient transfer from a substrate treated with a film forming formulation and transfer from a substrate treated with a non-film forming formulation.

Formulations A (Film Forming) and D (Non-Film Forming), described in the following table, were evaluated in this study:

TABLE 14

| Vehicle Ingredients | Formulation A (30 mg/ml testosterone, 5 mg/ml estradiol) | Formulation D (30 mg/ml testosterone, 5 mg/ml estradiol) |
|---|---|---|
| 0.1 g/L Tromethamine in Ethanol USP | 90.2 | 96.0 |
| Octisalate USP | 4.0 | 4.0 |

TABLE 14-continued

| Vehicle Ingredients | Formulation A (30 mg/ml testosterone, 5 mg/ml estradiol) | Formulation D (30 mg/ml testosterone, 5 mg/ml estradiol) |
|---|---|---|
| Eudragit ® S100 | 5.0 | — |
| Polyethylene glycol 400 | 0.8 | — |
| Vehicle Total | 100.0% w/w | 100.0% w/w |

Procedure:

The following procedure was used to evaluate each of formulations A and D above. 100 µl of the formulation was applied to a 4×5 cm glass coupon and allowed to dry for 15 minutes. A polyester swab was pressed against the film and translated back and forth in overlapping passes covering the entire surface. This step was repeated 7 additional times alternating coupon orientation by 90° and side of swab. The residue on the swab was extracted in 10 ml of ethanol. These recovered solutions were analyzed by HPLC and the recovered amounts of testosterone and estradiol were calculated by comparison to a standard of known concentrations.

The results of this study are described in the following table:

TABLE 15

| | Replicate results, % transferred | |
|---|---|---|
| Component | Formulation A | Formulation D |
| Testosterone | 0.3, 0.4 | 92.0, 90.3 |
| Estradiol | 0.2, 0.2 | 88.8, 87.4 |

Conclusion: The transfer of testosterone and estradiol from the film forming formulation was negligible and substantially less than the non-film forming formulation. This indicates that the film is effective as a barrier that limits skin to skin transfer of testosterone and estradiol.

Example 7: Washability Study

A washability study was performed to evaluate washability from a glass substrate with water for a film forming formulation containing Eudragit® S100 and polyethylene glycol 400 as well as the same formulation without polyethylene glycol 400 and the same formulation without Eudragit® S100 or polyethylene glycol 400.

The formulations described in the following table were evaluated in this study:

TABLE 16

| Vehicle Ingredients | Formulation A (30 mg/ml testosterone, 5 mg/ml estradiol) | Formulation D (30 mg/ml testosterone, 5 mg/ml estradiol) | Formulation E (30 mg/ml testosterone, 5 mg/ml estradiol) |
|---|---|---|---|
| 0.1 g/L Tromethamine in Ethanol USP | 90.2 | 96.0 | 91.0 |
| Octisalate USP | 4.0 | 4.0 | 4.0 |
| Eudragit ® S100 USP | 5.0 | — | 5.0 |
| Polyethylene glycol 400 | 0.8 | — | — |
| Vehicle Total | 100.0% w/w | 100.0% w/w | 100.0% w/w |

The following procedure was used for each of the three formulations above: 100 µl of the formulation was applied to a 4×5 cm area on a glass coupon and allowed to dry for 15 minutes. The coupon was dipped in warm water. The coupon was scrubbed with a damp sponge in circular motions for 30 seconds. The dipping and scrubbing steps were repeated. The coupon was allowed to dry. Residue remaining on coupons after washing was observed to determine whether the film was washed off.

No residue remained on the coupon for formulation A indicating that the formulation is washable. Residue remained on the coupon for formulation D and formulation E indicating that these formulations are not washable.

Conclusion: The film forming formulation had no remaining residue indicating that the film is washable with water.

Example 8: Breathability Study

A breathability study was performed to evaluate water vapor transmission rate through another film forming formulation. Formulation G (Film Forming), described in the following table, was evaluated in this study.

TABLE 17

| Ingredients | Formulation G |
|---|---|
| 0.1 g/L Tromethamine in Ethanol USP | 88.2 |
| Octisalate USP | 6.0 |
| Methacrylic Acid and Methyl Methacrylate Copolymer (1:2) USP-NF (Eudragit ® S100) | 5.0 |
| Polyethylene glycol (PEG 400) | 0.8 |
| TOTAL | 100.0% w/w |
| Testosterone USP | 120 mg |
| — | For Testosterone weight QS 1 ml with above solution |

Procedure: The formulation was applied to the surface of porous surgical tape (Transpore™, 3M, St. Paul, Minn.) membrane at 12.5 µl per cm² and allowed to dry. A water vapor impermeable container with an opening at the top was partially filled with water. The tape substrate was placed over the opening of the container with the film application area covering the opening. The container was stored in a humidity chamber at 37° C. in the presence of calcium chloride desiccant that maintained a low humidity within the chamber. Water loss from the container over time was determined gravimetrically by periodically measuring the container weight over a period of at least 48 hours, and a water vapor transmission rate per area was determined. Two reference control evaluations were performed—a non-occluded control with only the porous tape and an occluded control in which the porous tape was covered with non-porous packaging tape.

The sample film had a mean water vapor transmission rate of 1743 g/m²/24 hours, and this rate as a fraction relative to the non-occluded control was 0.80. The relative transmission result comes from the equation (sample mean rate-occluded control mean rate)/(non-occluded control mean rate-occluded control mean rate).

This high water vapor transmission rate relative to the non-occluded control indicates that the film is not obstructing water vapor transmission.

Conclusion: The second film forming formulation does not impede water vapor transmission when applied to a porous membrane. Thus, the breathability of the film forming formulation is sufficient to allow water to evaporate through the film.

Example 9: Crystallization Study

This study was performed to evaluate whether testosterone or estradiol crystallized from the film forming formulation following evaporation of the formulation solvent on a glass substrate, and to determine whether the film forming excipient or washability enhancer impact the crystallization of testosterone or estradiol.

The following formulations were evaluated.

TABLE 18

| Ingredients | Formulation A | Formulation D | Formulation E |
|---|---|---|---|
| 0.1 g/L Tromethamine in Ethanol USP | 90.2 | 96.0 | 91.0 |
| Octisalate USP | 4.0 | 4.0 | 4.0 |
| Methacrylic Acid and Methyl Methacrylate Copolymer (1:2) USP-NF (Eudragit ® S100) | 5.0 | — | 5.0 |
| PEG 400 | — | 0.8 | — |
| TOTAL | 100.0% w/w | 100.0% w/w | 100.0% w/w |
| Testosterone USP | 30 mg/ml | 30 mg/ml | 30 mg/ml |
| Estradiol USP | 5 mg/ml | 5 mg/ml | 5 mg/ml |

Procedure:

A Hamilton syringe was used to spray each formulation onto a 0.8 cm² silicon wafer plate. The target amount was 100 ul/20 cm². For formulation A, 10 μL and 60 samples were evaluated. For formulation D two 20 μL samples were evaluated. For formulation E 20 μL and 60 μL samples were evaluated. Each plate was then stored for 30 minutes at RT (22° C.)/~50% RH (ambient RH). For formulation A, samples were taken at 25 minutes for the 10 sample and at 30 minutes for the 60 μL sample. For formulation D samples were taken at 15 and 25 minutes. For formulation E samples were taken at 20 minutes for the 20 μL sample and at 30 minutes for the 60 μL sample.

Samples were collected using a spatula. The samples were evaluated by Two Dimensional powder X-ray diffractometry (2DPXRD). The instrument used was a D8 Discover, Bruker 2D X-ray diffractometer. Cobalt was used as the source and the collimator setting was 800 microns beam diameter. The results for each sample are shown in FIGS. 3-9.

Conclusions: For all formulations, evaluation by 2DPXRD indicates that the precipitate was amorphous. There were no discernible differences between formulations A, D and E (up to 30 minutes). Thus, all three formulations prevent crystallization of testosterone and estradiol following solvent evaporation.

What is claimed is:

1. A composition consisting of:
   a. about 0.01% w/w to about 10% w/w estradiol;
   b. about 0.1% w/w to about 25% w/w testosterone;
   c. one or more penetration enhancers selected from the group consisting of 1-dodecylazacycloheptan-2-one, Glycerol Monooleate, Isopropyl Myristate, Octisalate, Oleic Acid, and diethylene glycol monoethyl ether;
   d. one or more solvents selected from the group consisting of Acetone, Ethanol and Isopropyl Alcohol;
   e. about 1% to about 10% of one or more film forming excipients selected from the group consisting of Methacrylic Acid and Methyl Methacrylate Copolymer 1:1, Methacrylic Acid and Methyl Methacrylate Copolymer 1:2, Poly (butylmethacrylate-co-(2-dimethylaminoethyl) methacrylate-co-methyl methacrylate 1:2:1, Hypromellose, Hydroxypropyl Cellulose, and Ethyl Cellulose;
   f. one or more washability enhancers, wherein the washability enhancer is about 2% to about 30% the weight of the film forming excipient, and
   g. optionally, a fragrance, viscosity increasing agent, water, or combination thereof, wherein said film forming excipient (i) has a solubility in water, at a pH between 1 and 10, that requires 30 parts or less of water to dissolve one part of said film forming excipient, and (ii) has a solubility in ethanol that requires 30 parts or less of ethanol to dissolve one part of said film forming excipient; and wherein said composition is a sprayable liquid solution that forms a washable film when sprayed on skin, and wherein said composition can prevent crystallization of said estradiol and said testosterone when said composition is applied to skin.

2. The composition of claim 1, wherein said composition, when dried on a porous substrate, has a water vapor transmission rate, as a fraction compared to a non-occluded control, not less than 0.50 over a 48 hour period.

3. The composition of claim 1, wherein said composition further comprises tromethamine.

4. The composition of claim 1, wherein said penetration enhancer is octisalate, and said film forming excipient is Methacrylic Acid and Methyl Methacrylate Copolymer 1:1.

5. The composition of claim 1, wherein said composition contains estradiol in a concentration of about 5 mg/mL and testosterone in a concentration of about 30 mg/mL, and the volume of said composition is about 25 μL to about 300 L.

* * * * *